United States Patent [19]

Berger

[11] E Re. 30,677

[45] Reissued Jul. 14, 1981

[54] SILICONE CONTAINING BIS-THIOETHER AROMATIC AMINES

[75] Inventor: Abe Berger, Summit, N.J.

[73] Assignee: M&T Chemicals Inc., Woodbridge, N.J.

[21] Appl. No.: 137,405

[22] Filed: Apr. 4, 1980

Related U.S. Patent Documents

Reissue of:

[64] Patent No.: 4,139,547
Issued: Feb. 13, 1979
Appl. No.: 906,877
Filed: May 17, 1978

[51] Int. Cl.[3] ..... C07F 7/10

[52] U.S. Cl. ..... 556/423; 556/413; 556/425

[58] Field of Search ..... 556/423, 425, 413

[56] References Cited

U.S. PATENT DOCUMENTS

| | | | |
|---|---|---|---|
| 2,865,885 | 12/1958 | De Benneville et al. | 556/410 X |
| 3,660,454 | 5/1972 | Gornowicz et al. | 556/423 X |
| 3,678,089 | 7/1972 | Berger | 556/414 |
| 3,959,327 | 5/1976 | Pepe et al. | 556/413 X |
| 4,005,116 | 1/1977 | Griffiths | 556/412 |

FOREIGN PATENT DOCUMENTS 1062418 3/1967 United Kingdom .

*Primary Examiner*—Paul F. Shaver
*Attorney, Agent, or Firm*—Stanley A. Marcus; Donald G. Marion; Robert Spector

[57] ABSTRACT

A silicone containing bis-thioether aromatic amine has a chemical structure wherein an aromatic nucleus at each end of the chemical radical is chemically bonded to the remainder of the chemical radical by either sulfur, sulfoxide or sulfone.

5 Claims, No Drawings

SILICONE CONTAINING BIS-THIOETHER AROMATIC AMINES

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to amines which are suitable for making silicone containing polymer materials employed as wire coatings or as passivation and/or protective coatings for semiconductor devices.

2. Description of the Prior Art

The electrical industry is always seeking suitable coating materials which will improve the physical and/or electrical properties of electrical articles to which it is applied. The material must be one that is easily applied and cured in place. The material when cured must also be easily repairable when required and only a small amount of material be applied to the article to achieve the desirable electrical and chemical properties. Suitable coating materials may include a copolymer which when cured can be the reaction product of a silicon-free organic diamine, an organic tetracarboxylic dianhydride and a polysiloxane diamine. Any improvements in electrical and physical properties of coating materials which can be achieved by improving the process of making one or more of the ingredients is most desireable by industry.

Therefore, it is an object of this invention to provide a new and improved polysiloxane diamine suitable for use in making wire coatings and junction and/or protective coating materials for semiconductor devices.

Another object of this invention is to provide a new and improved silicone containing bis-thioether aromatic amine which enhances the antioxidant properties and thermal stability of coating materials made therefrom.

A further object of this invention is to provide a new and improved process for making the silicone containing bis-thioether aromatic amine.

Other objects of this invention will, in part, be obvious and will, in part, appear hereinafter.

In accordance with the teachings of this invention there is provided a new and improved amine for making polymer materials with improved antioxidant and thermal stability properties and a process for making the amine. The new amine is a silicone containing bis-thioether aromatic amine having the general formula

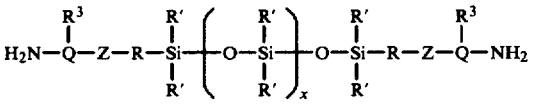

wherein

Q is an aromatic nucleus

Z is sulfur, sulfoxide or sulfone

R is a bivalent group or a functional bivalent group

R′ is a monovalent hydrocarbon radical or a functional hydrocarbon radical $R^3$ is a *hydrogen atom, a* hydrocarbon radical or a functional group such as a halogen, and x is 0 or greater.

The new amine is suitable for making polymers with improved physical properties for electrical wires and protective and/or junction coatings for semiconductor materials.

A preferred form of the new amine embodies sulfone for Z in the formula and imparts excellent thermal stability to polymers made from the amine.

DESCRIPTION OF THE INVENTION

I have discovered a silicone containing bis-thioether amine which is easy to formulate and which can improve the anti-oxidant and thermal stability properties of coating materials made therefrom. The new amine has the general formula:

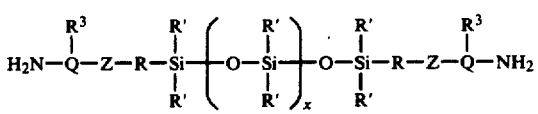

(I)

wherein

Q is an aromatic nucleus

Z is sulfur, sulfoxide or sulfone

R is a bivalent group or a functional bivalent group

R′ is a monovalent hydrocarbon radical or a functional hydrocarbon radical $R^3$ is a *hydrogen atom, a* hydrocarbon radical or a functional group such as a halogen, and x is 0 or greater.

A preferred form of the new amine of Formula (I) has sulfone as part of the general formula in order to produce polymer films which have high thermal stability as well as excellent anti-oxidant properties.

The preferred form of the new amine of Formula (I) may be made by charging a 3-necked flask with 43.28 parts of 50% aqueous sodium hydroxide solution, 112 parts dimethylsulfoxide (DMSO), 120 parts toluene and 68.75 parts p-amino-thiophenol. The reaction is brought to reflux in a nitrogen atmosphere with rapid agitation. The water of the charged ingredients (the aqueous hydroxide solution) and the water formed during the neutralization reaction is removed azeotropically and collected in a Dean Stork trap. The refluxing solvent is returned to the reaction mixture. The pot temperature, that is the temperature of the reaction mixture, climbs from an initial 110° C. to about 180° C. during a period of from 7 to 8 hours of stirring. At the end of this time period water is no longer evolved from the reaction mixture.

The reaction mixture is then cooled to about 80° C. At this temperature of about 80° C., 86.6 parts of bis(-chlorobutyl)tetramethyldisiloxane is added dropwise to the reaction mixture. The chemical reaction which occurs during the dropwise addition is slightly exothermic. Therefore the addition is controlled to retain the reaction temperature at about 80° C. Upon completion of the silane addition, the reaction is allowed to proceed at about 80° C. for a period of time which is usually overnight.

The reaction is monitored such, for example, as by use of a GC analytical means. When GC analysis indicates a new peak having a long retention time, the reaction is complete.

The reaction mixture is filtered and the solvents, toluene and DMSO, are removed under a reduced pressure of about 10 mm. The stripped mixture is distilled and the desired end product is recovered at a temperature of from about 310° C. to 315° C. at from 0.1 mm to 0.5 mm pressure. The chemical structure may be confirmed by suitable chemical analysis means such as IR on NMR. The structure of the recovered new amine of Formula (I) has the chemical name bis-(p-aminophenylthiobutyl)tetramethyldisiloxane. A yield of about 75 percent is achieved by this process.

The new amines of this invention [Formula (I)] are suitable for making a copolymer material which is the product of the condensation reaction of an organic diamine with one of the new amines with molar amounts of an organic dianhydride and having a general formula which is one selected from the group consisting of (aXII)

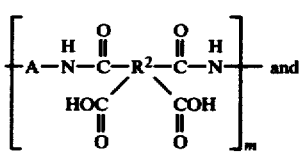

with from 0 to 99 mol percent intercondensed structure units of the formula:

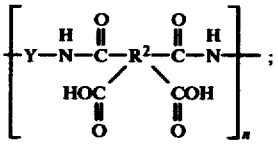

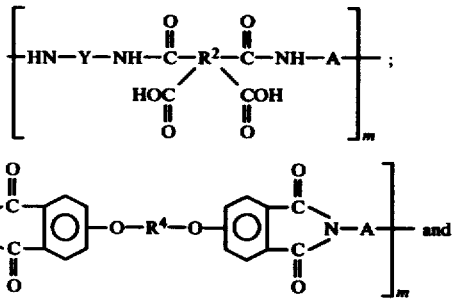

with from 0 to 99 mol percent intercondensed structure units of the formula:

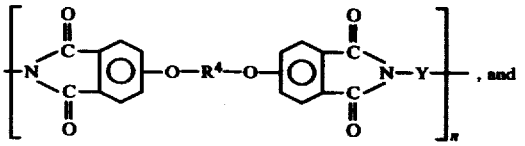

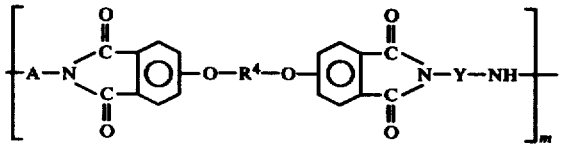

wherein

A is one of the new silicone containing bis-thioether aromatic amine of Formula (I)

$R^2$ is a tetravalent organic radical or an alkylene and/or an arylene dioxy-Bis (phenyline) radical defined by the following general formula:

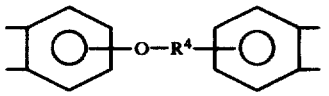

m and n are the same or different integers greater than 1 and preferably from 10 to 10,000 or more;

Y is a divalent silicon-free organic radical which is the residue of an organic diamine or a macrocyclic crown ether;

x is 0 or greater, and $R^4$ is a member selected from the group consisting of (1) a divalent organic radical and (2) divalent organic radicals of the general formula:

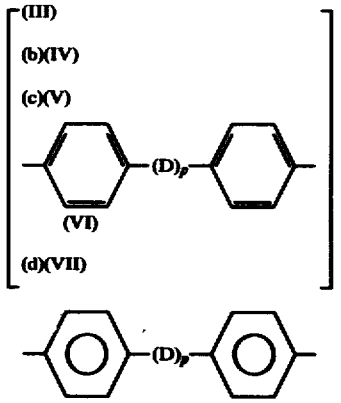

wherein

D is a member selected from the group consisting of divalent radicals of the formulas:

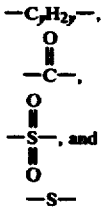

p is 0 or 1, y is a whole number from 0 to 5, and the divalent bonds of the —O—$R^4$—O— radical are equally situated on the phthalic anhydride end group, for example, in the 3,3'-positions or the 4,4'-positions.

The divalent organic radicals of (1) for $R^4$ of Equation V may be any of the following:

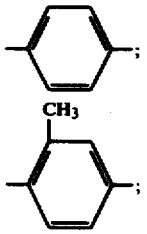

-continued

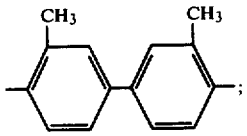

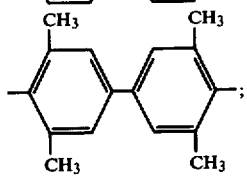

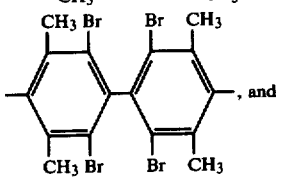

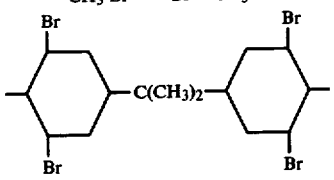

The above-mentioned block and random copolymer materials can be prepared by effecting reaction, in the proper molar proportions, of a mixture of ingredients comprising a silicone Bis-(ether aromatic amine), the structure of which is found in Formula I and a silicone-free diamino compound of the formula:

$$NH_2—Y—NH_2 \qquad \text{(VIII)}$$

with molar amounts of dianhydride of the formula:

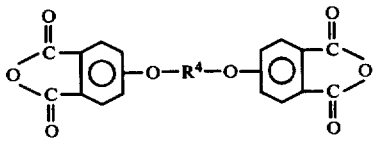

(IX)

wherein $R^4$ and Y have the meaning as given before.

Other organic tetracarboxylic dianhydrides containing no ether linkages can be added in an amount up to about 50%, by molar requirements, of the total anhydride requirements of the reaction system with the diamino functional compounds. For example, the mixture of ingredients may include a second tetracarboxylic dianhydride having the formula

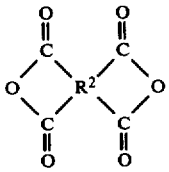

(X)

wherein $R^2$ has the meaning previously recited herein. Films resulting from the incorporation of the optional addition of a second ether-free dianhydride are more solvent resistant and more stable to attack by alkali, amines or hydrazine reagents. Thus the reaction product may additionally contain up to 50 mol percent of recurring structural units of the formula:

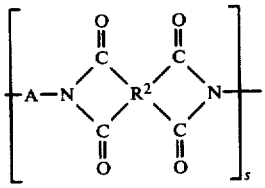

(XI)

with 1 to 99 mol percent intercondensed structural units of the formula:

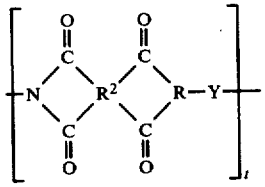

(XII)

wherein

R, R', $R^2$ and Y have the meaning as given before, and s and t are the same or different integers greater than 1 and preferably from 10 to 10,000 or more.

The diamines of Formula VIII are described in the prior art and are to a large extent commercially available materials. Typical of such diamines from which the prepolymer may be prepared are the following:

m-phenylenediamine;
p-phenylenediamine;
4,4'-diaminodiphenylpropane;
4,4'-diaminodiphenylmethane (hereinafter referred to as "methylenedianiline");
benzidine;
4,4'-diaminodiphenyl sulfide;
4,4'-diaminodiphenyl sulfone;
4,4'-diaminodiphenyl ether;
1,5-diaminophthalene;
3,3'-dimethylbenzidine;
3,3'-dimethoxybenzidine;
2,4-bis(β-amino-t-butyl)toluene;
bis(p-β-amino-t-butyl)phenyl ether;
bis(p-β-methyl-o-aminopentyl)benzene;
1,3-diamino-4-isopropylbenzene;
1,2-bis(3-aminopropoxy)ethane;
m-xylylenediamine;
p-xylylenediamine;
bis(4-aminocyclophexyl)methane;
decamethylenediamine;
3-methylheptamethylenediamine;
4,4-dimethylheptamethylenediamine;
2,11-dodecanediamine;
2,2-dimethylpropylenediamine;
octamethylenediamine;
3-methoxyhexamethylenediamine;
2,5-dimethylhexamethylenediamine;
2,5-dimethylheptamethylenediamine;
3-methylheptamethylenediamine;
5-methylnonamethylenediamine;
1,4-cyclohexanediamine;
1,12-octadecanediamine;
bis(3-aminopropyl)sulfide;
N-methyl-bis(3-aminopropyl)amine;

hexamethylenediamine;
heptamethylenediamine;
nonamethylenediamine;

and mixtures thereof. It should be noted that these diamines are given merely for the purpose of illustration and are not considered to be all inclusive. Other diamines not mentioned will readily be apparent to those skilled in the art.

The aromatic bis(ether anhydride) of Formula IX may include the following:

2,2-bis[4-(3,4-dicarboxyphenoxy)phenyl] propane dianhydride;
2,2-bis[4-(2,3-dicarboxyphenoxy)phenyl] propane dianhydride;
4,4'-(p-phenylenedioxy)diphthalic anhydride, and
3,3'-(p-phenylenedioxy)diphthalic anhydride.

The ether-free tetracarboxylic acid dianhydrides of Formula X, which is optional, may be defined in that $R^2$ is a tetravalent radical, for example, a radical derived from or containing an aromatic group containing at least 6 carbon atoms characterized by benzonoid unsaturation, wherein each of the 4 carbonyl groups of the dianhydride are attached to a separate carbon atom in the tetravalent radical, the carbonyl groups being in pairs in which the groups in each pair are attached to adjacent carbon atoms of the $R^2$ radical or to carbon atoms in the $R^2$ radical at most one carbon atom removed, to provide a 5-membered or a 6-membered ring as follows:

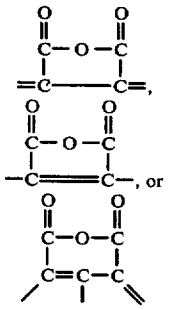

Illustrations of dianhydrides suitable for use in the present invention (with their reference designation in paranthesis) include:

pyromellitic dianhydride (PMDA);
2,3,6,7-napthalene tetracarboxylic dianhydride;
3,3',4,4'-diphenyl tetracarboxylic dianhydride;
1,2,5,6-napthalene tetracarboxylic dianhydride;
2,2',3,3'-diphenyl tetracarboxylic dianhydride;
bis(3,4-dicarboxyphenyl)sulfone dianhydride;
benzophenone tetracarboxylic acid dianhydride (BPADA);
perylene-1,2,7,8-tetracarboxylic acid dianhydride;
bis(3,4-dicarboxyphenyl)methane dianhydride, and aliphatic anhydrides such as cyclopentane tetracarboxylic dianhydride, cyclohexane tetracarboxylic dianhydride, butane tetracarboxylic dianhydride, and the like.

The following is an example of the use of one of the new silicone containing bis-thioether aromatic amines in making a polymer material:

To a reaction mixture consisting of 58.44 g 1,3-bis-(p-aminophenylthiobutyl)tetramethyldisiloxane and 29.94 g m-phenylenediamine in 636 g dry N-methyl-pyrrolidone and cooled to 0° C. was added portionwise, over a four hour period, 127.50 g benzophenonetetracarboxylic dianhydride. The solution became dark amber and its viscosity greatly increased toward the latter half of the reaction.

Upon complete anhydride addition, solution was not complete but stirring was maintained for 10 additional hours at ambient temperature. At this time, a dark amber clear viscous solution resulted which wet the sides of the flask well. The product obtained was a silicone polyamic acid precursor solution containing 30 mol percent of 1,3-bis-(p-aminophenylthiobutyl)tetramethyldisiloxane.

A sample of the above reaction product material in the form of a precursor solution was disposed on the surface of a glass slide to form a coating 0.2 mil in thickness. The coated slide was then placed in a furnace to effect a curing of the applied precursor solution material in the following manner:

2 hours at 135° C.±10° C.
2 hours at 185° C.±10° C.
2 hours at 250° C.±10° C.
½ hour at 300° C.±10° C.

After curing and upon removal of the control slide from the furnace, examination of the resulting film was performed. The cured film bonded very tenaciously to the glass slide. The coating still bonded tenaciously to the glass slide even after immersion in boiling water for a period of 6 hours. The cured coating material also had excellent anti-oxidant properties and exhibited good thermal stability up to the order of 450° C.

Cured films as obtained above have been found suitable for use as electrical wire coatings for motor and generator windings as well as for protective and/or junction coatings for semiconductor devices.

I claim as my invention:

1. A silicone containing bis-thioether aromatic amine having the general formula:

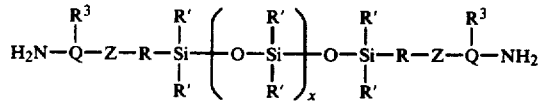

wherein

Q is an aromatic nucleus
Z is sulfur, sulfoxide or sulfone
R is a bivalent group or a functional bivalent group
R' is a monovalent hydrocarbon radical or a functional hydrocarbon radical
$R^3$ is a *hydrogen atom, a* hydrocarbon radical or a functional group, and
x is 0 or greater.

2. The silicone containing bis-thioether aromatic amine of claim 1 wherein

Z is sulfone.

3. A process for making a silicone containing bis-thioether aromatic amine having the general formula

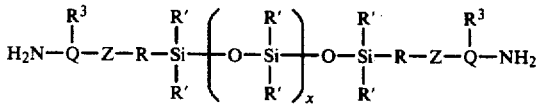

wherein

Q is an aromatic nucleus
Z is sulfur, sulfoxide or sulfone
R is a bivalent group or a functional bivalent group R′ is a monovalent hydrocarbon radical or a functional hydrocarbon radical $R^3$ is a *hydrogen atom, a* hydrocarbon radical or a functional group, and x is 0 or greater, comprising the process steps of (a) preparing a charge of toluene, aqueous sodium hydroxide solution, dimethylsulfoxide and a chemical compound containing a source of Z in the general formula for the amine to form a reaction mixture;

(b) bringing the reaction mixture to reflux temperature;

(c) maintaining the reaction mixture at reflux temperature while constantly agitating the reaction mixture;

(d) removing both the water introduced into the reaction mixture as part of the charge and the water formed during a chemical reaction occurring at the reflux temperature;

(e) cooling the reaction mixture to a predetermined temperature range after all of the water has been removed;

(f) adding a siloxane containing chemical compound to the reaction mixture while maintaining the temperature within the predetermined range;

(g) continuing the reaction for a period of time upon completion of the siloxane addition;

(h) stripping the toluene and diphenylsulfoxide, and (i) distilling the stripped reaction mixture to obtain the silicone containing bis-thioether aromatic amine of the general formula.

4. The process of claim 3 wherein the chemical compound containing the source of Z is p-aminothiophenol, the predetermined temperature range to which the reaction mixture is cooled is about 80° C., the siloxane containing chemical compound is bis(-chlorobutyl)tetramethyldisiloxane, the distilling temperature is from about 310° C. to about 315° C., and distilling is practised at a pressure of from about 0.1 mm to about 0.5 mm, and the amine recovered is bis-(p-aminophenylthiobutyl)-tetramethyldisiloxane.

*5. The silicone-containing bis-thioether amine of claim 1 wherein $R^3$ is hydrogen, Z is sulfur, R is butylene and R′ is methyl.*

* * * * *